United States Patent [19]
Zenoni et al.

[11] Patent Number: 5,663,330
[45] Date of Patent: Sep. 2, 1997

[54] PROCESS FOR THE SELECTIVE SULFOXIDE REDUCTION OF 3-HYDROXY CEPHEM AND 3-METHYLENE CEPHAM COMPOUNDS

[75] Inventors: Maurizio Zenoni, Paullo; Mario Leone, Pioltello; Giuseppe Alessandro Donadelli, Casalpusterlengo, all of Italy

[73] Assignee: ACS Dobfar S.p.A., Tribiano, Italy

[21] Appl. No.: 576,905

[22] Filed: Dec. 22, 1995

[30] Foreign Application Priority Data

Apr. 21, 1995 [IT] Italy .................................. MI95A0825

[51] Int. Cl.⁶ .................................................. C07D 499/04
[52] U.S. Cl. .................................................. 540/215
[58] Field of Search ................................. 540/215

[56] References Cited

U.S. PATENT DOCUMENTS

| | | | |
|---|---|---|---|
| 4,137,407 | 1/1979 | Murakami et al. | 544/228 |
| 4,695,627 | 9/1987 | Verweij et al. | 540/224 |

OTHER PUBLICATIONS

Chemical Abstracts, vol. 85, No. 15, AN 108653j, Oct. 11, 1976, JP-A-76 034 188, Mar. 23, 1976.

*Primary Examiner*—John M. Ford
*Attorney, Agent, or Firm*—Oblon, Spivak, McClelland, Maier & Neustadt, P.C.

[57] ABSTRACT

Process for selectively reducing cephalosporin sulfoxides of 3-hydroxy cephem and 3-methylene cepham compounds by treatment with a chlorinating agent in the presence of a solvent and a base, which are both inert to the chlorinating agent.

8 Claims, No Drawings

PROCESS FOR THE SELECTIVE SULFOXIDE REDUCTION OF 3-HYDROXY CEPHEM AND 3-METHYLENE CEPHAM COMPOUNDS

The present invention relates to a process for the selective sulfoxide reduction of 3-hydroxy cephem and 3-methylene cepham compounds, and more particularly to a process for the selective sulfoxide reduction of cephem compounds having a hydroxy group at the 3-position and an oxidized sulfur atom at the 1-position and of cepham compounds having a methylene group at the 3-position and an oxidized sulfur atom at the 1-position.

Sulfoxides in the chemistry of cephem derivatives, particularly cephalosporins, are of great importance, as clearly evidenced, for example, in "Chemistry and Biology of β-Lactam Antibiotics" Ed. Morin Academic Press New York 1982.

However, the importance of sulfoxides is just consequence of the importance of the intermediate compounds in the production of finished β-lactam antibiotics, wherein sulfoxides are converted to sulfides: it is therefore evident the importance of the availability of a selective method for reducing only the sulfoxide functionality in compounds of the type mentioned above.

Several general methods for reducing sulfoxides to sulfides are known, which employ a number of reagents [Org. Prep. Proced. Int. 9, 63–83 (1977); Kozuka Chem. Ind., 277 (1973); Synthesis, 138 (1978); J. Org. Chem., 48, 3667 (1983); J. Chem. Soc. C. 2424 (1969); Synthesis, 385 (1975); Chem. Ind., 277 (1973); Synthesis, 141 (1981); J. Org. Chem., 43, 4503 (1978)].

For the reduction of sulfoxide groups in cephem derivatives a smaller number of reagents are reported, in the practice almost exclusively $PCl_3$ in DMF ["Cephalosporins and Penicillins: Chemistry and Biology" (ed. Flynn), 183–254, Academic Press, New York; J. Org. Chem. 35, 2430 (1970); Canadian Patent 1099256] or acetyl chloride in the presence of a reducing agent ["J. Org: Chem:"., 35,2430 (1970)].

$PCl_3$ in DMF is very widely employed even in the industrial field, especially for the low cost of such materials: this method, however, presents the drawback of a side reaction, i.e. the chlorination of the substrate which is to be reduced.

On the Chemical Abstracts, Vol. 85, no. 15, 11 October 1976; abstract no. 108653j, page 464, column R, there is described a method by which it is possible to reduce an oxidized sulfur atom at the 1-position only of cephem compounds having a methyl substituted group at the 3-position. Later on the U.S. Pat. No. 4,137,407 disclosed a similar analogy method by which it was possible to reduce the oxidized sulfur atom (to give the corresponding sulfide) at the 1-position of a cepham compound having both a hydroxy group and a methyl group at the 3-position: together with such reduction, however, also the hydroxy group is released from the 3-position and the cepham ring is transformed to the corresponding cephem ring.

Therefore, the teachings of the above referred method are that when the sulfur oxide is reduced, also the hydroxy group at the 3-position is removed (U.S. Pat. No. 4,137,407) with simultaneous change of the ring structure; while the reduction of the oxidized sulfur atom a the 1-position can take place without change of the ring structure if at the 3-position of the cephem ring there is a methyl substituted group (Chemical Abstracts).

What stated hereabove is confirmed by what is disclosed in the EP-A-137534, where practically the same reduction method on the oxidized sulfur atom at the 1-position of a cephem ring is disclosed as being effectively carried out on a very large number of cephem compounds in which, however, at the 3-position of the ring there is never an hydroxy group alone.

According to the present invention it has now been surprisingly found that it is possible to selectively reduce the oxidized sulfur atom at the 1-position of cephem compounds having only a hydroxy group at the 3-position and of cepham compounds having simply only an unsubstituted methylene group at the 3-position, without causing any other changes to take place in such compounds.

This and other objects are reached by a process characterized in that cephem compounds having a hydroxy group at the 3-position and an oxidized sulfur atom at the 1-position, and respectively cepham compounds having a methylene group at the 3-position and an oxidized sulfur atom at the 1-position are treated with a chlorinating agent in the presence of a proton acceptor and an essentially dry solvent, which are both essentially inert to the chlorinating agent, at temperatures between −65° C. and +50° C., the stoichiometries of the chlorinating agent and of the proton acceptor being both in the range between 1 and 5 equivalents and the concentration of cephem and respectively cepham sulfoxide in the solvent being in the range between 5% and 20% w/v to give the corresponding cephem and respectively cepham sulfide.

It has been surprisingly found that this sulfoxide reduction can be carried out very selectively with regard to other functional groups (such as amide, ester, conjugated or non-conjugated double bond, aromatic or aliphatic nitro group, ketone even in the enolic form) present in the cephalosporin substrates and that the ketone or enol functionalities do not interact during the reduction of sulfoxide to sulfide.

As chlorinating agent, $PCl_3$, $PCl_5$, $COCl_2$, $SO_2Cl_2$ and $SOCl_2$ can be suitably used.

As proton acceptors, inert to the chlorinating agent, can be employed organic bases, such as tertiary amines, both aromatic and aliphatic, f.e. triethylamine, diisopropylethylamine, pyridine, picolines, particularly a-picoline, lutidines, particularly a-lutidine, N-methylmorpholine, quinoline, quinolidine, N-methylpyrrolidine; olefins, f.e. amylene, hexene, cyclooctene, undecene, and epoxy compounds, f.e. ethylene oxide and propylene oxide.

As solvent inert to the chlorinating agent are suitable the halogenated solvents, such as methylene chloride, dichloromethane, carbon tetrachloride, chloroform, freon, dichloroethane; ethers, such as ethyl ether, isopropyl ether, tetrahydrofuran; esters, such as ethyl acetate, butyl acetate, dimethyl carbonate, aromatic hydrocarbons, such as benzene, toluene, nitrobenzene, and linear or branched, saturated or partially unsaturated, $C_5$–$C_{10}$ aliphatic hydrocarbons.

The preferred temperature fro the reduction is in the range between −10° C. and +30° C. and the preferred stoichiometries of the chlorinating agent and the proton acceptor are in the range between 2 and 3 equivalents.

The following examples are not limitative, but only illustrative of the reduction process of some cephem sulfoxide, a few procedure variants being included.

In the examples, the NMR spectra were obtained by Bruker AC 300 MHz , IR spectra by FT 8101M Shimazu, melting points by Buchi 535. Reactions were monitored by HPLC with columns RP $C_{18}$ 5m Endcapped, at 270 nm. The mobile phase was 40% THF, 60% 0,01M phosphate buffer.

Starting materials and products as reference standards were prepared according to the literature ["Chemistry and Biology of b-Lactam Antibiotics" Vol 1, Ed. Morin e Gorman, 1982) Academic Press New York; Helv. Chim. Acta, 57, 1919–1935 (1974)].

EXAMPLE 1

10 g (20 mmoles) of sulfoxide of 3-hydroxy-7-phenylacetamido-cephalosporanic acid, paranitrobenzyl ester, are completely dissolved in 150 ml of dry methylene chloride (KF=0.05%), cooled to $-10°$ C. and, then, 3.5 ml (40 mmoles) $PCl_3$ and 4.0 (40 mmoles) of a-picoline are added. The mixture is stirred on an ice bath for three hours. The organic phase is washed with 2×300 ml of cold water, dried on magnesium sulfate and concentrated under vacuum to residue. The residue is taken up in 100 ml of ethyl acetate and warmed to 40° C. to obtain a precipitate of crystalline product. After two hours the suspension is cooled to room temperature and filtered. 7.2 g of paranitrobenzyl ester of 3-hydroxy-7-phenylacetamido-cephalosporanic acid are obtained with a global yield of 73%. The product shows a HPLC pattern of 94%, with a melting point +203° C.

IR, KBr tablet ($cm^{-1}$): 3400 (amide, OH); 3085, 1775 (b-lactam), 1655, 1605, 1522.

NMR $CDCl_3$ (ppm from TMS): 11.57 (1H,s., enol OH.); 8.3/7.39 (9H, m aromatic); 6.21 (1H, d, NH, amide); 5.74/5.71 (1H, d.d., 7-hydrogen); 5.56/5.08 (2H, q., PNB methylene); 5.08/5.07 (1H, d., 6-hydrogen) 3.73/3.72 (2H, q., phenylacetamido methylene); 3.58/3.30 (2H, q., 2-methylene).

EXAMPLE 2

The procedure of Example 1 is repeated, but 150 ml of toluene are employed instead of dichloromethane.

The reaction is carried out at room temperature. The yield in solution is 63%.

EXAMPLE 3

The procedure of Example 1 is repeated with 9.3 g (20 mmoles) of sulfoxide of 3-methylene-7-phenylacetamido-cefam-4-carboxylic acid, paramethoxybenzyl ester. The raw product (7 g) is crystallized from methanol, whereby 5 g of the corresponding sulfide are obtained (56% yield) with a HPLC pattern of 98% and a melting point 135° C.

IR, KBr tablet ($cm^{-1}$): 3308 (amide); 3030/2836; 1770 (b-lactam); 1724; 1659; 1612; 1516.

NMR $CDCl_3$ (ppm from TMS): 7.35/6.87 (9H, m., aromatic); 6.19 (2H, d., NH, amide); 5.66/5.62 (1H, d.d., 7-hydrogen); 5.33/5.32 (1H, d., 6-hydrogen); 5.18 (1H, s., 4-hydrogen); 5.16/5.05 (4H, m., exomethylene+PMB methylene); 3,81 (3H, s., methoxy); 3.61 (2H, s., phenylacetamido methylene); 3.60/3.08 (2H, q., 2-methylene).

We claim:

1. A process for the selective sulfoxide reduction of 3-hydroxy cephem and respectively 3-methylene cepham compounds, characterized in that cephem compounds having a hydroxy group at the 3-position and an oxidized sulfur atom at the 1-position, and respectively cepham compounds having a methylene group at the 3-position and oxidized sulfur atom at the 1-position is treated with a chlorinating agent in the presence of a proton acceptor and an essentially dry solvent, which are both essentially inert to the chlorinating agent, at temperatures between −65° C. and +50° C., the stoichiometries of the chlorinating agent and of the proton acceptor being both in the range between 1 and 5 equivalents and the concentration of cephem and respectively cepham sulfoxide in the solvent being in the range between 5% and 20% w/v to give the corresponding cephem and respectively cepham sulfide.

2. Process according to claim 1, characterized in that said proton acceptor inert to the chlorinating agent is selected from the group of organic bases, tertiary amines, olefins, epoxy compounds.

3. Process according to claim 2, characterized in that said proton acceptor is selected from the group of triethylamine, diisopropylethylamine, pyridine, picolines, lutidines, N-methylmorpholine, quinoline, quinolidine, N-methylpyrrolidine, amylene, hexene, cyclooctene, undecene, ethylene oxide and propylene oxide.

4. Process according to claim 1, characterized in that said solvent is selected from halogenated, ether, ester and aromatic hydrocarbon solvents.

5. Process according to claim 4, characterized in that said solvent is selected from the group of methylene chloride, dichloromethane, carbon tetrachloride, freon, dichloroethane, ethyl ether, isopropyl ether, tetrahydrofuran, ethyl acetate, butyl acetate, dimethyl carbonate, diethyl carbonate, benzene, toluene, nitrobenzene, saturated or partially insaturated $C_5$–$C_{10}$ hydrocarbons.

6. Process according to claim 1, characterized in that said chlorinating agent is selected from the group of $PCl_3$, $PCl_5$, $COCl_2$, $SO_2Cl_2$, $SOCl_2$.

7. Process according to claim 1, characterized in that the reduction is carried out at temperatures in the range between −10° C. and +30° C.

8. Process according to claim 1, characterized in that the stoichiometries of the chlorinating agent and the proton acceptor are in the range between 2 and 3 equivalents.

* * * * *